United States Patent [19]

Allison

[11] 4,016,868
[45] Apr. 12, 1977

[54] GARMENT FOR IMPEDANCE PLETHYSMOGRAPH USE

[76] Inventor: Robert D. Allison, Rte. 4, Box 4325, Belton, Tex. 76513

[22] Filed: Nov. 25, 1975

[21] Appl. No.: 635,259

[52] U.S. Cl. .................... 128/2.1 E; 128/2.05 V; 128/2.1 Z; 128/379; 128/418; 128/DIG. 4
[51] Int. Cl.² .................................... A61B 5/04
[58] Field of Search ........ 128/2.05 V, 2.1 Z, 2.1 E, 128/2.06 E, 379, 380, 381, 382, 384, 404, 410, 411, 416, 417, 418, DIG. 4

[56] References Cited

UNITED STATES PATENTS

| | | | |
|---|---|---|---|
| 206,474 | 7/1878 | Morel | 128/416 |
| 710,429 | 10/1902 | Collins et al. | 128/416 |
| 3,134,891 | 5/1964 | Hyer | 128/410 |
| 3,396,264 | 8/1968 | Murphy et al. | 128/382 |
| 3,534,727 | 10/1970 | Roman | 128/2.06 E |
| 3,542,010 | 11/1970 | Love | 128/2.1 E |
| 3,835,839 | 9/1974 | Brown | 128/2.05 V |
| 3,835,840 | 9/1974 | Mount | 128/2.05 V |
| 3,871,359 | 3/1975 | Pacela | 128/2.1 Z |
| 3,874,368 | 4/1975 | Asrican | 128/2.1 Z |

*Primary Examiner*—Robert W. Michell
*Assistant Examiner*—Lee S. Cohen
*Attorney, Agent, or Firm*—Wofford, Felsman, Fails & Zobal

[57] ABSTRACT

An apparatus for applying electrodes to a body for impedance plethysmograph measurements, comprising a garment of elastic fabric which fits tightly over the body. Conductive strips encircle the sleeves for the arms, gloves for the hands, and the sections for the legs, in parallel pairs, at selected intervals. Conductive strips are also located on the back of the garment, adjacent the thorax region and on the hood covering the neck and the head. The conductive strips are elastic fabric impregnated with a conductive material and woven into the nonconductive portions of the garment. Instruments may be clipped to the various conductive strips, which are insulated electrically from each other, for making blood flow measurements.

12 Claims, 5 Drawing Figures

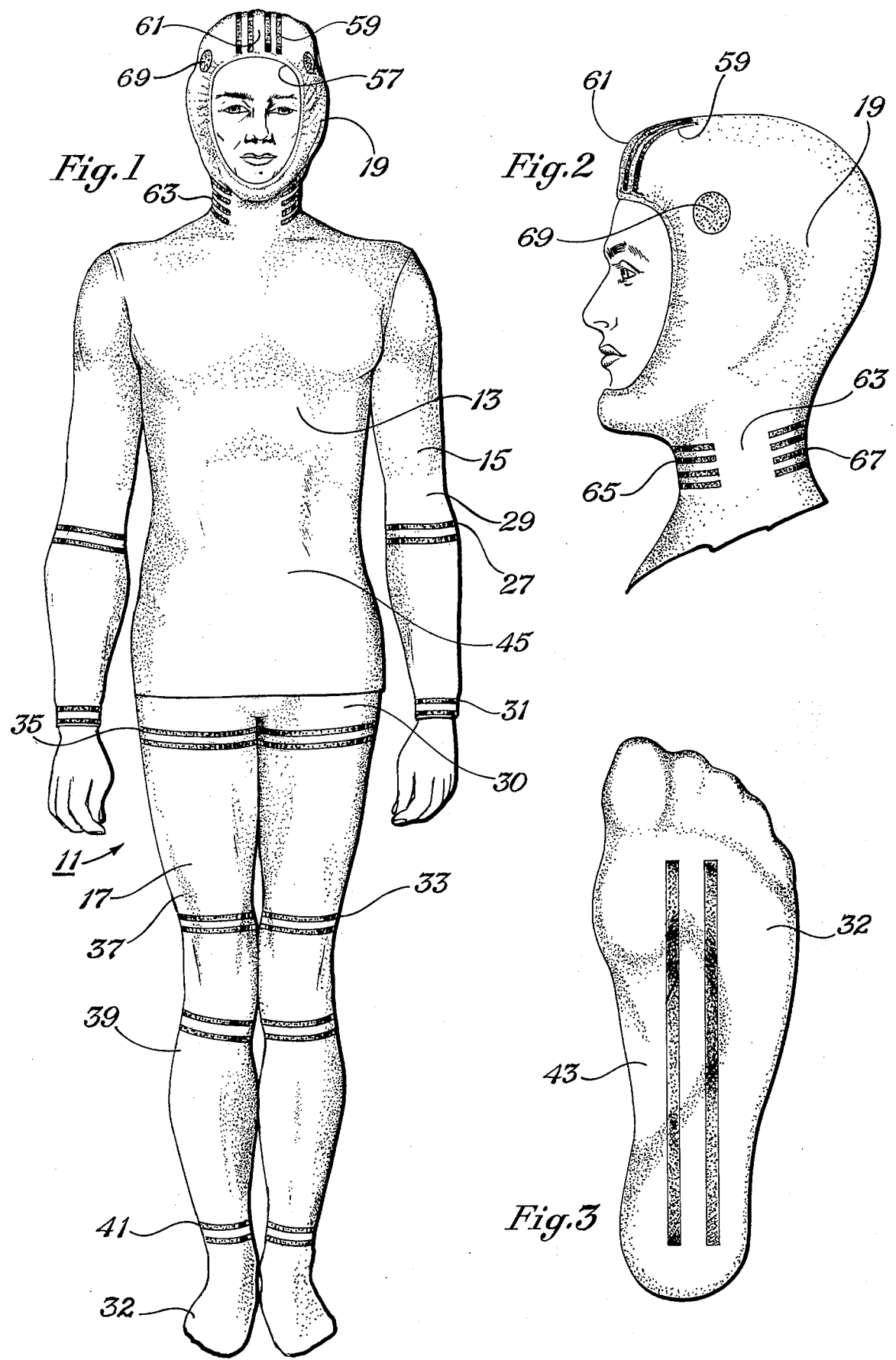

GARMENT FOR IMPEDANCE PLETHYSMOGRAPH USE

BACKGROUND OF THE INVENTION

1. Field of the Invention

This invention relates in general to devices for non-invasively measuring blood flow in the human body, and in particular to a garment to be worn for applying electrodes to a body for impedance plethysmograph measurements.

2. Description of the Prior Art

Impedance plethysmographs are known in the art. The plethysmograph measurement non-invasively determines blood pulse volume and blood flow in a segment of the body. Four electrodes are placed on the skin adjacent the particular portion of the body to be measured. The outer pair of the electrodes introduces constant current, while the inner pair detects the variations in the voltage. Instruments used for impedance plethysmograph are described in U.S. Pat. Nos. 3,340,867 and 3,835,840.

Generally the electrodes are conductive metal rings. One difficulty associated with making the plethysmograph measurements is that the rings must fit tightly against the skin. Because limb and body size varies considerably, a large variety of rings are required. Also a conductive ointment at the interface is normally needed to provide better contact and reduce noise.

A tightly fitting vest, having electrodes attached, is described in U.S. Pat. No. 3,534,727. The vest is designed for use in vector-cardiology measurements while physically exercising, and has several large electrodes spaced around the upper region of the user's body. The electrodes are comprised of conductive fabric stretched over layers of padding and semirigid material to provide a contour to fit the body. The electrodes are detachably attached to the inside of a nylon vest and wired together. Repositioning of the electrodes are necessary for different body sizes. Such a vest lacks the necessary spacing of electrodes and is unnecessarily complex for impedance plethysmograph measurements.

SUMMARY OF THE INVENTION

It is accordingly a general object of the invention to provide an improved apparatus for applying electrodes to a body for impedance plethysmograph measurements. It is a further object to provide an improved garment having integral electrodes spaced for use in impedance plethysmograph that will fit tightly on limbs and bodies of a large variety of sizes without rearrangement of the electrodes.

In accordance with these objects, a garment is provided comprised of elastic fabric that is designed to fit over the body. At selected intervals, the fabric has strips integral with it that are impregnated with a conductive material, such as silver. The strips are spaced in parallel pairs and serve as electrodes for the impedance plethysmograph instruments to be attached. A tight fit for a large variety of sizes is provided, as well as uniform spacing an electrode placement.

BRIEF DESCRIPTION OF THE DRAWINGS

FIG. 1 is a front elevational view of a person wearing a garment made in accordance with this invention.

FIG. 2 is a side elevational view of the head of the person of FIG. 1 and the hood portion of the garment.

FIG. 3 is a bottom elevational view of the foot of the person of FIG. 1 and the sock portion of the garment.

DESCRIPTION OF THE PREFERRED EMBODIMENT

Figure 4:
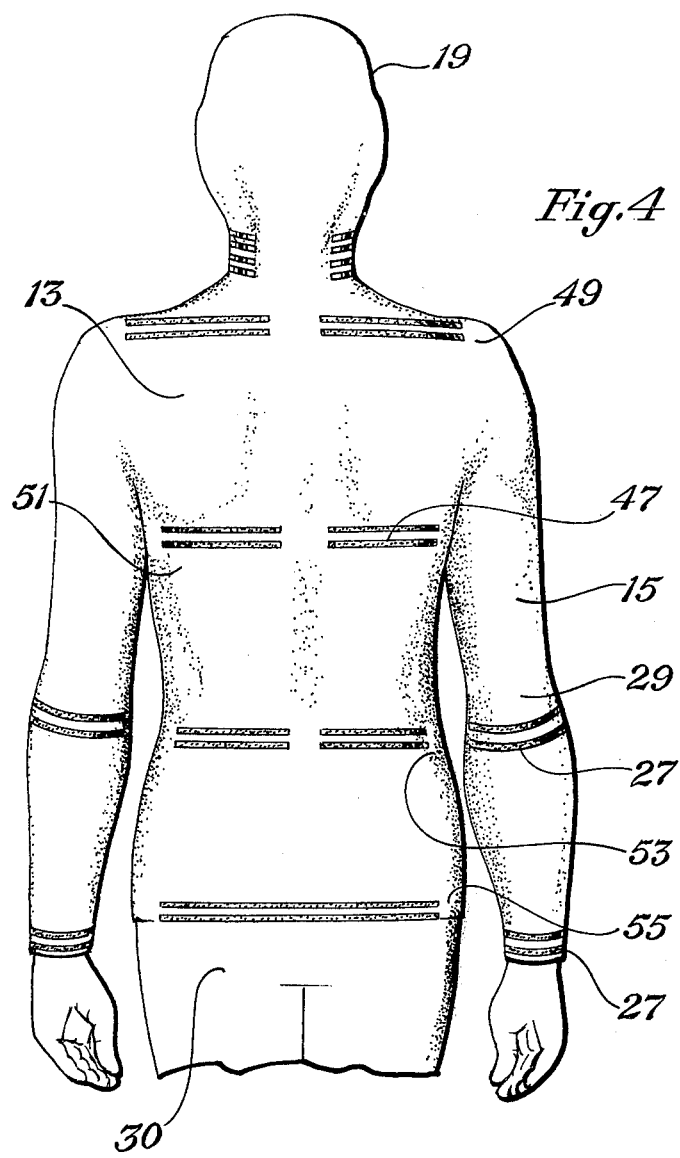
FIG. 4 is a partial rear elevational of the person of FIG. 1 and the back of the shirt portion of the garment.

FIG. 1 shows the electrode apparatus or garment 11 as typically worn. The garment 11 covers all of the body except the face, being made up of a shirt section 13, sleeve section 15, leg section 17, hood section 19, and gloves 21. The garment is of a lightweight, elastic material or fabric, such as nylon.

Sleeves 15 may be sewed to the shirt 13, as shown in the drawing, or remain separate. Each sleeve 15 is cylindrical and of a size to fit tightly on a user's arm. One end of the sleeve 15 may be formed into a glove 21, FIG. 5, or detached as in the drawings. Glove 21 has finger 23 and thumb 25 portions and is adapted to fit tightly over the hand.

Figure 5:
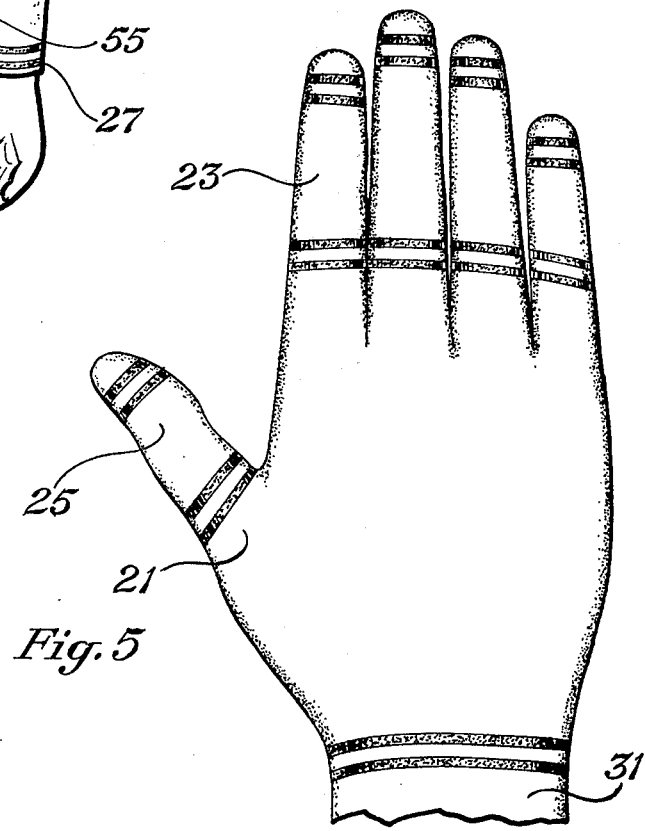
FIG. 5 is a top elevational view of the hand of the person of FIG. 1 and the glove portion of the garment.

A plurality of conductive segments or strips 27 are located on the sleeve 15 and glove 25. The strips 27 on the sleeves are in pairs, with each strip parallel to the other strip in the pair, and each strip encircling the sleeve perpendicular to the longitudinal axis of the arm. A pair of the strips are located on the portion of the sleeve slightly below the user's elbow 29, and a pair adjacent the wrist 31. Referring to FIG. 5, two pairs of the strips encircle the portion of the glove covering the user's thumb 25 and each portion covering the fingers 23, one pair at the top and the other the base. The strips on the glove are perpendicular to each longitudinal axis of each thumb or finger. A pair of strips also encircle the portion of the glove covering the user's wrist 31.

The sections that form the legs 17 are cylindrical and of a length and size to fit tightly over the user's leg. The sections are formed together to define a pair of trousers 30. The bottoms of each leg section are in the form of a sock 32 for fitting tightly over the user's foot. Strips 33, similar to the arm and glove strips 27, encircle the leg sections in parallel pairs at the portions covering the upper thigh 35, slightly above the knee, designated as 37, slightly below the knee, designated as 39, and at the ankle 41. The strips on the leg are perpendicular to the longitudinal axis of the leg. On the bottom of the foot 43, FIG. 3, a pair of parallel strips run the longitudinal length of the foot.

The shirt 13 is of a pullover type, having an aperture for the neck, and is adapted to be fitted closely over the upper or thorax region of the body. No conductive strips are on the front side 45 of the shirt, however there are several strips 47 on the back side, FIG. 4. Strips 47 are in parallel pairs and run perpendicular to the longitudinal axis of the body. Two pairs are located at the portion covering the shoulders 49, two pairs at the chest 51, two pairs at the waist 53, and one pair at the hips 55. Each pair at the shoulder 49, chest 51, and waist 53 is aligned with its other pair but separated or insulated by a nonconductive portion in the center, for separately measuring the right and left sides of the body. The shirt 13 is not attached to the trousers 30, but normally the sleeves 15 are connected to the shirt.

A hood 19, FIGS. 1 and 2, is connected to the shirt 13 for covering the user's head. The hood 19 has an aperture, designated as 57, for exposing the face. The hood has a plurality of strips 59. Two pairs of the strips begin at the edge of aperture 57 and extend parallel to the longitudinal axis of the body over the forehead 61, terminating on top of the head. Four pairs of the strips are located on each side of the portion covering the neck 63. The strips run parallel to each other in each pair and are perpendicular to the longitudinal axis of the body. On each side, two pair are in the portion under the chin 65, at the top and bottom of the neck, and two pairs are at the back of the neck 67, at the top and bottom. The strips around the neck may be considered as four conductive rings encircling the neck with nonconductive portions in each ring directly under the center of the chin, at the center at the back of the neck, and at the center of each side. Circular conductive patches 69 are located on the hood 19 adjacent the user's temple on each side.

All of the strips in the garment are approximately ⅛ inch wide, with the strips in each pair being parallel to each other and approximately ½ inch apart. All of the strips are elastic fabric such as nylon, impregnated with a conductive metal, preferably silver. Other metals such as aluminum, gold or copper may serve also. The impregnated strips are woven into the garment fabric at the selected intervals as the garment is being manufactured, presenting a uniform interior and exterior surface. The remaining fabric of the garment is nonconductive, consequently each strip and patch is insulated from all others. Since the strips are woven integrally with the garment, they are not detachable.

In operation, all or any portion of the garment such as the trousers 30, sleeves 15, or shirt 13, are pulled over the limbs or body. Conventional impedance plethysmograph instruments are clipped to four strips covering the portion of the body desired to be measured. Normally the person is immobile while being measured. After a record is made of that segment, other segments may be measured as well. The full garment would enable measurements to be made of cerebral circulation, cardiac output (stroke volume versus heart rate), segmental limb blood flow, digit blood supply, and respiratory gas volume (by breathing).

It is readily apparent that an invention having significant advantages has been provided. Impedance plethysmograph measurement may be made quickly since the electrodes are positioned properly and tightly merely by placing the garment over the body or limb. Interface ointment is not required, and only a few sizes of garments are needed to fit the majority of persons. Multiple measurements could be made at the same time.

While the invention has been shown in only the preferred form, it should be apparent that it is not limited to this particular form but is susceptible to various changes and modifications without departing from the spirit or the scope thereof. For example, it may be desired to delete or separate portions of the garment, such as the hood, sock, or glove. Spacing, size and the number of strips may be varied.

I claim:

1. An apparatus for providing electrical contact with a body for impedance plethsmograph measurements comprising:
   a garment of nonconductive elastic fabric for clothing tightly a portion of the body; and
   a plurality of electrodes, insulated electrically from each other and located at selected intervals in pairs for the attachment of instruments to measure blood flow in the body; the electrodes being elastic fabric impregnated with conductive material and woven into the nonconductive portions of the garment, providing a uniform interior and exterior surface of the garment.

2. The apparatus of claim 1 wherein the electrodes are conductive strips and the garment comprises:
   a shirt for fitting over the upper part of the user's body, with a plurality of the strips located on the back of the shirt;
   a pair of sleeves carried at each side of the shirt for fitting over the user's arms with a plurality of the strips encircling the sleeves at selected intervals;
   a glove carried below the lower end of one sleeve for fitting over the user's hand with finger sections for fitting over the user's fingers, and with a plurality of the strips encircling the finger sections;
   a pair of trousers carried below the shirt for fitting over the user's legs with a plurality of the strips encircling each leg section of the trousers at selected intervals;
   a sock for fitting over the user's foot and attached to the end of each leg section of the trousers, with a plurality of the strips located on the bottom of the sock; and
   a hood carried above the shirt for covering the user's head, and having an aperture for exposing the face, with a plurality of strips being located on the hood at selected areas.

3. A garment for providing electrical contact with a limb of a body for impedance plethysmograph measurements comprising:
   a cylindrical section of elastic nonconductive fabric shaped for closely fitting over a limb of a user's body; and
   a plurality of electrodes formed interior and exterior of the section to allow electrical connection with the skin of the limb; the electrodes insulated electrically from each other and located on the section at selected intervals in pairs; the electrodes being elastic fabric impregnated with conductive material and woven into the nonconductive portions of the section.

4. The garment of claim 3 wherein the section is a sleeve shaped for fitting over the user's arm defining an intermediate section covering the vicinity of the user's elbow and an end section at the user's wrist and wherein the electrodes are conductive strips parallel to each other, a pair of the strips encircling the sleeve on the intermediate section and a pair on the end section.

5. The garment of claim 3 wherein the section is shaped for fitting over the user's leg defining end sections covering the user's upper thigh and ankle and intermediate sections above and below the user's knee, and wherein the electrodes are conductive parallel strips with a pair of the strips encircling the section at each end section and two pair of the strips encircling the section in the intermediate sections, one pair in the intermediate sections adapted to be in contact with the user's leg directly above the knee and the other pair in the intermediate sections adapted to be in contact with the user's leg directly below the knee.

6. The garment of claim 3 further comprising:
   a sock of elastic nonconductive fabric, for fitting over a foot, attached to one end of the section; and one pair of parallel conductive strips located on the bottom of the sock and formed interior and exterior of the sock to allow electrical connection with the skin of the foot; the strips on the sock being elastic fabric impregnated with conductive material and woven into the nonconductive portions of the sock.

7. A garment for providing electrical contact with a hand for impedance plethysmograph measurements comprising:
   a glove of elastic nonconductive fabric for fitting around a user's hand having finger sections for covering fingers; and a plurality of electrodes in pairs formed interior and exterior of the glove to allow electrical connection with the skin of the hand and located on theglove at selected intervals; the electrodes being elastic fabric impregnated with conductive material and woven into the nonconductive portions of the section.

8. The garment of claim 7 wherein the electrodes are parallel conductive strips, and a pair of the strips encircle the glove at its base for contact with the hand adjacent the user's wrist, and two pairs of the strips encircle each finger section .

9. A garment for providing electrical contact with a body for impedance plethysmograph measurement comprising:
   a shirt of elastic nonconductive fabric for closely fitting over the upper part of a user's body; and a plurality of electrodes insulated electrically from each other and located at selected intervals in pairs along the back of the shirt; the electrodes being elastic fabric impregnated with conductive material and woven into the nonconductive portions of the shirt, providing a uniform interior and exterior surface of the garment.

10. The garment of claim 9 wherein the electrodes are parallel conductive strips, with two pairs of the strips located at the top of the back of the shirt adapted to be adjacent the user's shoulders, with four pairs of the strips located intermediate the top and bottom of the back of the shirt, two pair adapted to be adjacent the user's back and two pair adapted to be adjacent the waist, one pair at each said location being on the left side and the other on the right side, insulated from each other in the center, and wherein a single pair of the strips is located at the bottom of the back of the shirt adapted to be adjacent the hips extending across both sides, all of the pairs running perpendicular to the longitudinal axis of the shirt.

11. The garment of claim 9 further comprising:
   a hood of elastic nonconductive fabric for fitting over a user's head attached to the shirt; the hood having an aperture in the front for exposing the user's face, and a plurality of conductive strips formed interior and exterior of the hood to allow electrical connection with the skin of the user; the strips being separated electrically from each other and located on the neck and head coveringportions of the hood at selected intervals in parallel pairs for enabling the measurement of cerebral circulation; the strips on the hood being elastic fabric impregnated with conductive material and woven into the nonconductive portions of the hood.

12. The garment of claim 11 wherein
two pairs of the strips are located directly above the aperture for contact with the body adjacent the forehead; and wherein at least two pairs of the strips are located on each side of the base of the hood for contact with the body adjacent the neck; and further comprising a circular conductive patch on each side of the aperture for contact with the user's body adjacent the temples and formed interior and exterior of the hood to allow electrical connection; the patches being elastic fabric impregnated with conductive material and woven into the nonconductive portions of the hood.

* * * * *